United States Patent [19]

Schreyer et al.

[11] 4,159,925

[45] Jul. 3, 1979

[54] PROCESS FOR ISOLATING PROPYLENE GLYCOL DIESTERS IN THE PREPARATION OF PROPYLENE OXIDE

[75] Inventors: Gerd Schreyer; Rolf Wirthwein, both of Hanau; Karl-Hermann Reissinger, Leverkusen; Jörg Krekel, Essen, all of Fed. Rep. of Germany

[73] Assignees: Bayer Aktiengesellschaft, Leverkusen; Deutsche Gold- und Silber-Scheideanstalt vormals Roessler, Frankfurt am Main, both of Fed. Rep. of Germany

[21] Appl. No.: 858,319

[22] Filed: Dec. 9, 1977

Related U.S. Application Data

[63] Continuation of Ser. No. 678,827, Apr. 28, 1976, abandoned.

[30] Foreign Application Priority Data

Apr. 30, 1975 [DE] Fed. Rep. of Germany ....... 2519291

[51] Int. Cl.$^2$ ...................... B01D 3/14; C07D 301/02
[52] U.S. Cl. .......................................... 203/28; 203/73; 203/74; 260/348.37
[58] Field of Search ...................... 260/348.25, 348.37; 203/73, 74, 69, 60, 67, 68, 38, 8, 28, 29; 568/868

[56] References Cited

U.S. PATENT DOCUMENTS

| 3,335,179 | 8/1967 | Null et al. ............................... 203/69 |
| 3,654,094 | 4/1972 | Yamagishi et al. ............. 260/348.37 |

FOREIGN PATENT DOCUMENTS 880337  9/1971  Canada ................................ 260/348.22

Primary Examiner—Wilbur L. Bascomb, Jr.
Attorney, Agent, or Firm—Sprung, Felfe, Horn, Lynch & Kramer

[57] ABSTRACT

Process for isolating propylene glycol diacarboxylates in the preparation of propylene oxide by reaction of propylene with a solution of percarboxylic acid in an organic solvent, the boiling point of which is lower than that of the carboxylic acid which corresponds to the percarboxylic acid used as the epoxidizing agent, and higher than that of propylene oxide, separation, by distillation, of the reaction mixture which essentially contains propylene oxide, the carboxylic acid corresponding to the percarboxylic acid used as the epoxidizing agent and one or more of the by-products propyleneglycol, propylene glycol monocarboxylate and propylene glycol dicarboxylate as well as propylene and the organic solvent, into a fraction containing propylene oxide and propylene and a fraction containing the carboxylic acid, the by-products mentioned and the organic solvent and further separation of the fractions into the individual components by distillation. The fraction containing the carboxylic acid, one or more of the by-products propylene glycol, propylene glycol monocarboxylate and propylene glycol dicarboxylate, and the organic solvent is distilled in a column at pressures of 1.5 to 6 bars and with an average residence time of 10 to 90 minutes in the sump. The organic solvent is removed as the top product and the carboxylic acid and the corresponding propylene glycol dicarboxylate is obtained as the sump product. From the sump product the propylene glycol dicarboxylate is isolated in a manner which is in itself known.

10 Claims, 1 Drawing Figure

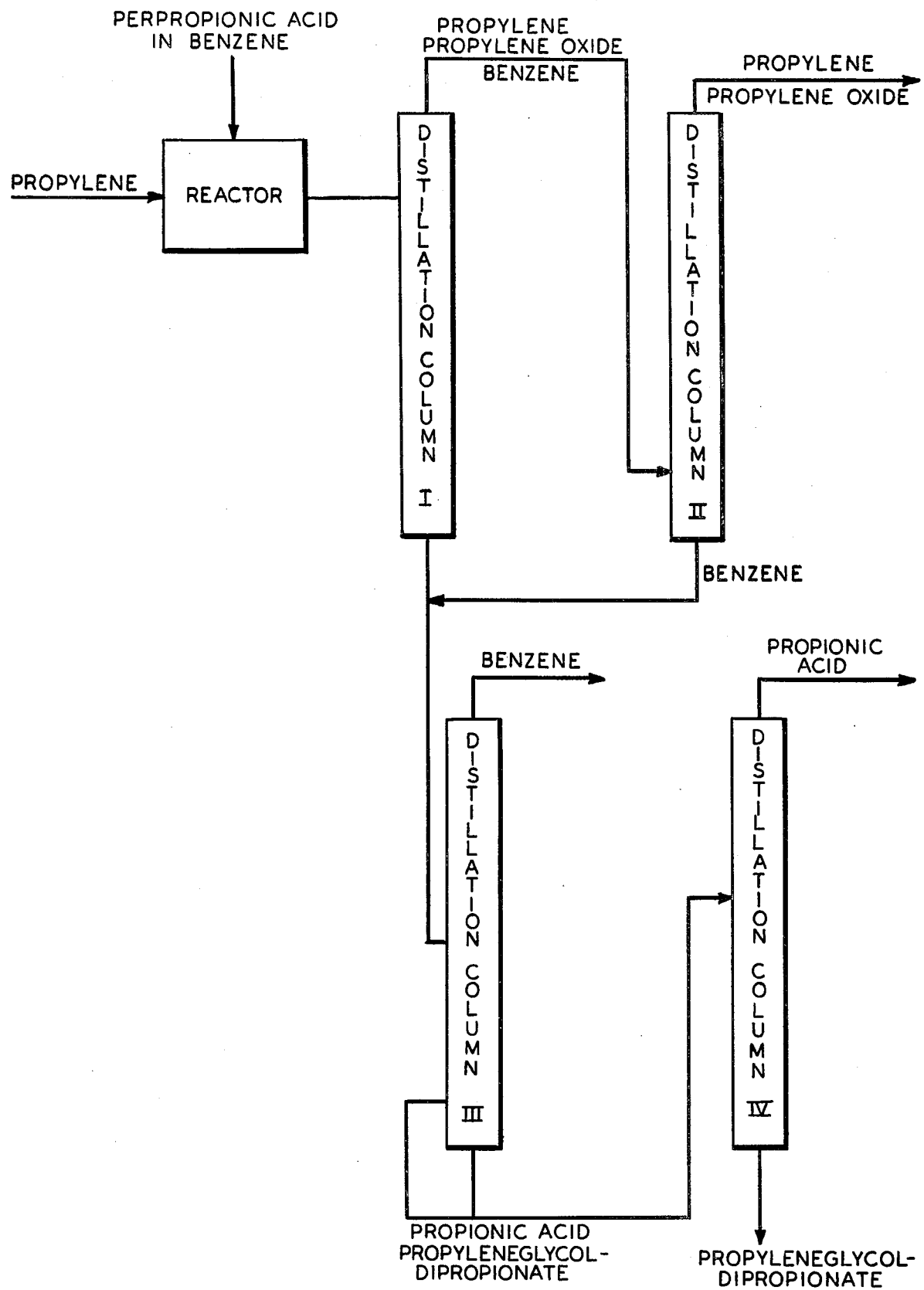

PROCESS FOR ISOLATING PROPYLENE GLYCOL DIESTERS IN THE PREPARATION OF PROPYLENE OXIDE

This is a continuation, of application Serial No. 678,327, filed Apr. 28, 1976 and now abandoned.

The present invention relates to a process for isolating propylene glycol diesters in the preparation of propylene oxide by reaction of propylene with an organic solution of a percarboxylic acid. Propylene glycol diesters are used as solvents for polymers or as non-toxic inhibitors for bacterial growth (U.S. Pat. No. 2,446,505).

It has long been known to epoxidise propylene with the aid of a percarboxylic acid to give propylene oxide (Prileshayev, Ber. dtsch. chem. Ges. 42, 4811 (1909)). D. Swern gives a comprehensive more recent review of this reaction in "Organic Peroxides," Wiley Interscience 1971, Volume 2, pages 355 to 533, especially pages 375 to 378. The percarboxylic acid is generally employed in the form of an organic solution for the epoxidation of propylene. (D. Swern, loc. cit., page 377, lines 28 to 29). Considerable amounts of by-products, such as propylene glycol, propylene glycol monoesters and propylene glycol diesters, readily form in this reaction for the preparation of propylene oxide from propylene. This is the case especially when water, a carboxylic acid (generally the carboxylic acid corresponding to the percarboxylic acid) or mineral acids are present in the organic percarboxylic acid solution (for example U.S. Pat. No. 3,350,422, column 2, lines 5 to 11; and also DT-OS (German Published Specification) No. 1,923,392, page 2, lines 19 to 25).

These contaminants which promote the formation of the by-products mentioned are generally unavoidable in the organic percarboxylic acid solutions used for the epoxidation. Water is always present, for example from the preparation of the percarboxylic acid. Thus, for example, there is a possibility of isolating peracetic acid or perpropionic acid as a solution in an inert organic solvent, for example in ethyl acetate or acetone, from the oxidation of acetaldehyde or propionaldehyde respectively (German patent specification No. 1,201,324), various by-products being formed, including water (N. A. Sokolova and others, Zh. Fiz. Khim 35, page 850 (1961) and Russian Journal of Physical Chemistry, Volume 35 (1961), pages 415 to 419, especially page 415, right-hand column, final paragraph).

If the percarboxylic acid is prepared from hydrogen peroxide and the corresponding carboxylic acid, in general percarboxylic acid solutions are obtained which also contain water and frequently also mineral acids.

For example, according to the process of DT-AS (German Published Specification) No. 1,043,316, a percarboxylic acid solution is obtained which contains the whole of the catalyst required for reaction of the percarboxylic acid with hydrogen peroxide. In detail, the process is to react acetic acid or propionic acid with aqueous hydrogen peroxide in the presence of sulphuric acid in a water-immiscible solvent and azeotropically to distil off the solvent water and part of the water formed during the reaction. In this process the resulting organic solution of the percarboxylic acid contains the acid catalyst used in the reaction, for example sulphuric acid (DT-AS (German Published Specification) No. 1,043,316, Example 1).

Another means of preparing organic solutions of percarboxylic acids from carboxylic acids and hydrogen peroxide is to react a corresponding carboxylic acid, in the presence of an acid catalyst, with hydrogen peroxide in aqueous solution and subsequently to extract the reaction mixture, which is formed, with an organic solvent. A process of this type is described, for example, in DOS (German Published Specification) No. 2,141,156, according to which an organic solution of percarboxylic acids having 2 to 4 carbon atoms is obtained by reaction of the corresponding carboxylic acid with aqueous hydrogen peroxide and subsequent extraction with a hydrocarbon or a chlorinated hydrocarbon. The percarboxylic acid solutions obtained contain 0.8 to 4.1% of water (DOS (German Published Specification) No. 2,141,156, Example 2).

It is apparent that with such extraction procedures organic solutions of percarboxylic acids are obtained which contain water and, if a soluble acid catalyst is present in the starting solution to be extracted, also an acid catalyst. Of course, amounts of unreacted carboxylic acid are also always present.

In order, when using this type of organic solutions of percarboxylic acids for the epoxidation of propylene to give propylene oxide, as far as possible to suppress the formation of the by-products propylene glycol, propylene glycol monoesters and propylene glycol diesters, which is due to the presence of water, a carboxylic acid and mineral acids, it has been attempted, on the one hand, to remove, as completely as possible, the contaminating water or mineral acid which promote the formation of these by-products; on the other hand, the process design conditions during the reaction and when working up the reaction mixture have been so selected that, as far as possible, these side reactions do not occur.

Azeotropic dehydration has been proposed in order to obtain percarboxylic acid solutions which are dehydrated to the desired degree (DOS (German Published Specification) No. 2,141,156). However, it must be pointed out that the required degree of dehydration of percarboxylic acid solutions cannot be achieved without considerable expenditure. Thus, it is stated, for example, in DOS (German Published Specification) No. 1,618,625, page 3, final paragraph, to page 4, first line: "The use of an anhydrous reaction mixture is desired, but the preparation of solutions of performic acid having less than 0.3% of water is neither simple nor economically tenable. The use of a reaction mixture which contains only a small amount of water is preferred."

The formation of the by-products mentioned can also be suppressed to a certain degree by excluding water and mineral acid as far as possible in the epoxidation reaction of propylene (DOS (German Published Specification) No. 1,618,625, page 5, lines 10 to 14); however, the side reactions which lead to propylene glycol, propylene glycol monoester and propylene glycol diester cannot be completely stopped. For example, according to Example 3 of DT-OS (German Published Specification) No. 1,618,625, the yield of propylene oxide, relative to percarboxylic acid consumed, is only 85%. The reason for this is that, on the one hand, the organic percarboxylic acid solutions can generally not be employed in the absolutely anhydrous state in the epoxidation and, on the other hand, even when water and mineral acid are completely excluded during the epoxidation, the carboxylic acid, which corresponds to the percarboxylic acid and which necessarily forms in the course of the reaction, can be added onto propylene oxide, the oxirane ring being opened, as is shown in equation (1).

wherein
R denotes a hydrocarbon radical.

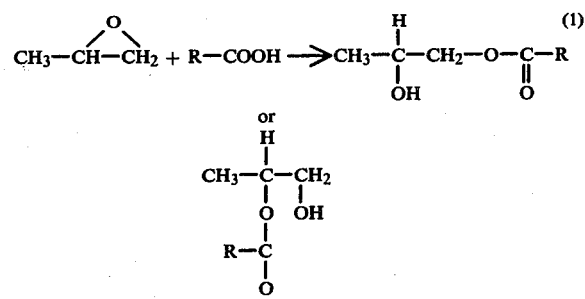

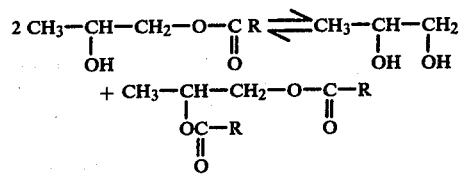

The glycol monoester formed by this opening of the propylene oxide ring can itself react further to give propylene glycol and propylene glycol diester, as is shown in equation (2) which follows:

$$2\ CH_3-CH-CH_2-O-C\ R \rightleftharpoons CH_3-CH-CH_2$$
$$\quad\quad|\quad\quad\quad\quad\quad\|\quad\quad\quad\quad\quad|\quad\quad|$$
$$\quad\ OH\quad\quad\quad\quad O\quad\quad\quad\quad OH\ OH$$
$$+\ CH_3-CH-CH_2-O-C-R$$
$$\quad\quad\quad\quad|\quad\quad\quad\quad\quad\|$$
$$\quad\quad\quad OC-R\quad\quad O$$
$$\quad\quad\quad\quad\|$$
$$\quad\quad\quad\quad O$$

As is known, an equilibrium between glycol monoester on the one hand and glycol and glycol diester on the other hand is set up in this reaction (DOS (German Published Specification) No. 2,425,844, pages 8 and 9, linking paragraph).

It can be seen from equations (1) and (2) that a mixture of propylene glycol, propylene glycol monoester and propylene glycol diester as by-products must always be expected when propylene oxide is prepared from propylene and percarboxylic acid, even if the reaction is carried out with very pure percarboxylic acid solutions.

The process design conditions in the reaction also influence the formation of the by-products mentioned and there has been no lack of effort so to select the conditions when carrying out the process industrially that the formation of by-product is prevented as far as possible.

In this context, it is proposed in British patent specification No. 1,105,261 to use a series of closed reaction loops, in which mixing of reaction product with the starting substances is largely prevented, for carrying out the reaction of a non-aqueous solution of peracetic acid with propylene. However, even under these conditions 2.5 mol % of propylene glycol monoacetate and a further 2.5 mol % of other higher-boiling by-products are formed (British patent specification No. 1,105,261, page 3, lines 63 to 68).

In the process of DT-OS (German Published Specification) No. 1,923,392 it is said that a reduction in the formation of the products from side-reactions is achieved when propylene is introduced in the form of bubbles into the reaction system (a peracetic acid solution), a reaction system consisting of a multiplicity of reaction zones (in practice a multi-stage bubble column) being used. However, in this case also, the formation of the by-products mentioned cannot be completely suppressed (DOS (German Published Specification) No. 1,923,392, page 14, lines 19 and 20).

However, the glycol and glycol ester by-products which have been mentioned not only form during the reaction between propylene and the percarboxylic acid but can also form during working up of the reaction mixture containing the propylene oxide (for example DOS (German Published Specification) No. 2,013,877, page 3, lines 9 to 16).

In order as far as possible to eliminate this increased formation of by-product during working up, an epoxidation mixture containing propylene oxide, propylene, acetic acid, a solvent and the by-products is fed, for example according to the process of German patent specification No. 1,802,241, continuously to a first distillation column, in which propylene and propylene oxide are distilled off over the top and then fed to a second distillation for separating propylene oxide and propylene. The solvent and the acetic acid can be isolated from the sump of the first distillation column by redistillation, by-products having higher boiling points, such as propylene glycol, propylene glycol monoacetate and polypropylene glycol acetates, which may in part emanate from the epoxidation and in part have been formed during the distillation by side-reactions, being obtained as the residue. According to Example 1 and 3 of German patent specification No. 1,802,241, 4.4 to 6.2 percent by weight of such high-boiling ester by-products, relative to the propylene oxide charged into the distillation, are obtained (German patent specification No. 1,802,241, column 3, lines 2 and 3; column 4, lines 24 to 26, and column 2, lines 28 to 41).

The problem of the formation of propylene glycol, propylene glycol monoester and propylene glycol diester during the preparation of propylene oxide from propylene with the aid of a percarboxylic acid can be summarised by stating that although it is possible, by using an organic solution, of a percarboxylic acid, which is as far as possible absolutely anhydrous and free from mineral acid and by selecting specific process design conditions for the reaction and for the subsequent working up of the reaction mixture containing propylene oxide, to depress the formation of the said by-products, it is not possible completely to prevent this. However, since industrial propylene oxide plants as a rule are very large production units, the formation of only a few percent of a mixture of propylene glycol, propylene glycol monoester and propylene glycol diester, for example 1 to 3 mol % of the amount of propylene oxide, in absolute terms can signify a considerable amount, the working up and further use of which can prevent difficulties. It is a particular disadvantage that the product obtained is always a mixture of the three by-products mentioned, which are derived from propylene glycol, and not a product which is at least substantially homogeneous.

A process has now been found for isolating propylene glycol dicarboxylates in the preparation of propylene oxide by reaction of propylene with a solution of a percarboxylic acid in an organic solvent, the boiling point of which is lower than that of the carboxylic acid which corresponds to the percarboxylic acid used as the epoxidising agent, and higher than that of propylene oxide, separation, by distillation, of the reaction mixture which essentially contains propylene oxide, the carboxylic acid corresponding to the percarboxylic acid used as the epoxidising agent and one or more of the by-products propylene glycol, propylene glycol monocarboxylate and propylene glycol dicarboxylate as well as propylene and the organic solvent, into a fraction containing propylene oxide and propylene and a fraction containing the carboxylic acid, the by-products mentioned and the organic solvent and further separation of these fractions into the individual components by distillation, which is characterised in that the fraction containing the carboxylic acid, one or more of the by-products propylene glycol, propylene glycol monocarboxylate and propylene glycol dicarboxylate, and the organic solvent, is distilled in a column at pressures of 1.5 to 6 bars and with an average residence time of 10 to 90 minutes in the sump, the organic solvent being removed as the top product and the carboxylic acid and the corresponding propylene glycol dicarboxylate being obtained as the sump product, from which the propylene glycol dicarboxylate is isolated in a manner which is in itself known.

BRIEF DESCRIPTION OF DRAWING

The invention can be understood when reference is made to the accompanying drawing which is a flow diagram of a process for the preparation of propylene oxide, which flow diagram shows the separation of propylene glycol dipropionate from the reaction product.

The process according to the invention can be employed in the preparation of propylene oxide by reaction of propylene with solutions of very diverse percarboxylic acids, that is to say for isolating the dicarboxylates of propylene glycol which correspond to the particular different percarboxylic acids. For example, the percarboxylic acids mentioned in D. Swern "Organic Peroxides," Volume I, Chapter VI, page 313 et seq. can be employed. Percarboxylic acids with 1 to 4 carbon atoms are particularly suitable. Acids which may be mentioned individually are performic acid, peracetic acid, perpropionic acid and the perbutyric acids. Peracetic acid, perpropionic acid and perisobutyric acid are very particularly suitable. However, percarboxylic acids which are substituted, for example by chlorine, fluorine or a nitro or alkoxy group, are also suitable. Examples which may be mentioned individually are monofluoroperacetic acid, trifluoroperacetic acid, 1-fluoroethanepercarboxylic acid, 2-chloroethane-1-percarboxylic acid, 2-fluoropropane-1-percarboxylic acid, 1-fluoropropane-1-percarboxylic acid, 3-fluoropropanepercarboxylic acid and 2-chloropropane-2-percarboxylic acid. Aromatic per-acids, such as perbenzoic acid, p-nitrobenzoic acid and monoperphthalic acid can also be used. The use of perpropionic acid is very particularly preferred.

In principle, all the compounds which are essentially inert under the conditions of the reaction and which have a boiling point which is higher than that of propylene oxide and lower than that of the carboxylic acid corresponding to the percarboxylic acid used are suitable as solvents for the per-acids. In general, the boiling point of the solvent is above 37° C. The upper limit for the boiling point of a suitable solvent is generally at about 220° C. However, in individual cases a solvent having an even higher boiling point can also be used. Usually the boiling point of the solvent used for the percarboxylic acid is in the range from about 40° to 150° C., for example between 60° and 120° C.

Suitable solvents which may be mentioned are: hydrocarbons, such as alkanes with 5 to 10 carbon atoms, cycloalkanes, such as cyclohexane, methylcyclohexane or ethylcyclohexane, aromatic hydrocarbons, such as benzene, toluene, xylene, ethylbenzene, chlorobenzene or dichlorobenzene, chlorinated hydrocarbons, such as methylene chloride, chloroform, 1,2-dichloroethane, 1,2-dichloropropane or chlorobenzene, esters of carboxylic acids containing 1 to 4 carbon atoms with alcohols containing 1 to 5 carbon atoms, such as ethyl formate, propyl formate, methyl acetate, ethyl acetate, isopropyl acetate, butyl acetate, methyl propionate, ethyl propionate, methyl butyrate, ethyl butyrate or ethyl isobutyrate. Particularly suitable solvents are chloroform, methylene chloride, methyl acetate, ethyl acetate and benzene. Benzene is used preferentially.

Solutions of percarboxylic acids in a solvent mixture can also be employed for carrying out the epoxidation reaction within the scope of the process according to the invention. It is also possible to render solutions of percarboxylic acids in a solvent which is less suitable for the epoxidation of propylene, for example triisooctyl phosphate, accessible to the process by adding a more suitable solvent.

The concentration of the percarboxylic acid in the organic solution can vary within wide limits. The upper limit is given by the explosibility of such solutions, which increases with rising concentration of the percarboxylic acid. Customary concentrations are, for example, 5 to 50 percent by weight of percarboxylic acid. Appropriately, a stabiliser is added to the percarboxylic acid solution. Examples of suitable stabilisers are partially esterified phosphorus-containing acids or the salts thereof, for example $Na_5(2\text{-ethylhexyl}_5\text{-}(P_3O_{10})_2$. The stabiliser is frequently present in an amount of 50 to 500 mg/kg of percarboxylic acid solution; the usual amount is 80 to 160 mg/kg.

The reaction between propylene and the organic percarboxylic acid can be carried out according to the customary methods. The reaction can be carried out in a homogeneous liquid phase. A heterogeneous reaction mixture (for example gaseous/liquid) can also be used. The reaction is carried out at normal pressure or at elevated pressures of up to, for example, 50 bars. A suitable pressure range is 2 to 30 bars. The reaction temperature is generally 0° to 120° C., preferably 20° to 100° C.

The molar ratio of propylene to percarboxylic acid can be varied within wide ranges. It is appropriate to employ propylene in excess. For example, the reaction is carried out with a propylene excess of 0.01 to 8.00 mols, relative to the percarboxylic acid.

All the customary equipment, such as stirred kettles or tube reactors of very diverse dimensions with regard to diameter and length, can be used as the reactor system for the reaction of propylene with the percarboxylic acid. A cascade of very diverse reactor units, for example of kettles, loop reactors or reaction loops, with, for example, 2 to 10 units, can also be used.

In general the reaction is carried out in such a way that the percarboxylic acid is reacted as completely as possible.

The composition of the mixture obtained from the reaction can also vary within wide ranges. The propylene oxide content is, for example, 1 to 50 percent by weight, preferably 3 to 25 percent by weight. The concentration of carboxylic acid corresponding to the percarboxylic acid employed can accordingly also be 1 to 50 percent by weight, preferably 3 to 30 percent by weight. As can be seen from the descriptions of the processes disclosed hitherto, the content of the by-products propylene glycol, propylene glycol monoester and/or propylene glycol diester can, depending on the purity (water, mineral acid and carboxylic acid content) and on the reaction conditions, be up to about 25 mol percent of the amount of propylene oxide formed. However, it is also possible, without difficulty, to obtain an even larger amount of the by-products by optionally adding water or mineral acid. However, the conditions of the reaction are generally so selected that only the unavoidable amount of these by-products is formed. This is frequently 1 to 10, usually about 2 to 5, mol percent of the amount of propylene oxide formed. The amount of solvent is generally 20 to 90 percent by weight, but in specific cases amounts above or below these limits can also be used. The reaction mixture generally still contains unconverted propylene in accordance with its solubility.

Generally, the reaction mixture is worked up by distillation by taking off propylene and propylene oxide together over the top in a first distillation, the solvent, the carboxylic acid and the by-products derived from propylene glycol being obtained as the sump phase. Another possible procedure is to take part of the solvent over the top with the propylene and the propylene oxide. By separating the top product, which essentially contains propylene, propylene oxide and solvent if appropriate, propylene oxide is obtained in a known manner, the other components being separated off.

The sump product from the first distillation, which contains the carboxylic acid, the solvent and the by-products derived from propylene glycol, is now again distilled, according to the invention, at a pressure of 1.5 to 6 bars and with an average residence time of 10 to 90 minutes in the sump, the organic solvent being taken off as the top product and the carboxylic acid and the corresponding propylene glycol dicarboxylate being obtained as the sump product from this second distillation column. The pressure in the distillation column is preferably 2.5 to 4 bars and preferentially 2.8 to 3.2 bars. In general, the sump temperature is about 130° to 250° C., preferably 150° to 220° C. and preferentially 160° to 190° C. The temperature at the top is likewise determined by the pressure and also by the boiling point of the solvent. The temperature at the top of the column is usually approximately up to 160° C., preferably 100° to 140° C.

The fractionation column is generally designed in such a way that substantially pure solvent is obtained at the top of the distillation column. Small amounts of carboxylic acid, for example less than 1 percent by weight, are possible. Appropriately, the conditions are so selected that the top product contains less than 0.3 percent by weight, preferably less than 0.1 percent by weight, of carboxylic acid.

When the distillation is carried out according to the invention virtually only propylene glycol dicarboxylate is formed instead of the propylene glycol/propylene glycol monoester/propylene glycol diester by-product mixture. The water of esterification produced in these reactions is removed over the top together with the solvent and condensed. Part of the condensate is fed, appropriately after separating off the water, as reflux into the column. The reflux ratio is generally 0.2 to 10, preferably 0.3 to 5 and preferentially 0.5 to 2.0.

In addition to the propylene glycol diester, the carboxylic acid is present in the sump. In addition, small amounts of solvent and of higher-boiling components may be present. The amount of solvent is, for example, less than 1 percent by weight, usually less than 0.3 percent by weight.

In general an average residence time of at least 10 minutes is required to guide the formation of by-product as completely as possible in the direction of propylene glycol dicarboxylate. Usually a residence time of 90 minutes is sufficient. In many cases an average residence time of 20 to 40 minutes is appropriate.

All the industrial equipment which is customarily used is suitable as the evaporator unit for the distillation column. Appropriately, reboilers or circulation reboilers are used. The known fractionation units, such as trayed columns or packed columns can be used as the columns.

Particular attention must be paid to the sump material because of the corrosive properties of the carboxylic acids. The solution to this problem is known. Suitable materials are high grade stainless steels which, in addition to iron, essentially also contain chromium and nickel. Examples of high grade stainless steels which may be mentioned are a material with the DIN designation 1,4571, which, in addition to iron, contains 17.5 percent by weight of chromium, 11.5 percent by weight of nickel, 2.25 percent by weight of molybdenum and also up to 2 percent by weight of manganese, up to 1 percent by weight of silicon, up to 0.1 percent by weight of carbon and small amounts of titanium, or a material which, in addition to iron, contains 25 percent by weight of chromium, 25 percent by weight of nickel, 2.25 percent by weight of molybdenum and up to 2 percent by weight of manganese, up to 1 percent by weight of silicon, up to 0.06 percent by weight of carbon and also small amounts of titanium and which is designated, according to DIN, by the number 1,4577. The material, which is designated according to DIN by the number 2,4812 and which, in addition to nickel, contains 16% by weight of molybdenum and 16% by weight of chromium, or a material which is designated by DIN 1,4439 and which, in addition to iron, contains 16.5 to 18.5 percent by weight of chromium, 12.5 to 14.5 percent by weight of nickel, 4 to 5 percent by weight of molybdenum as well as 0.12 to 0.22 percent by weight of nitrogen and up to 0.04 percent by weight of carbon, up to 0.1 percent by weight of silicon, up to 2 percent by weight of manganese, up to 0.03 percent by weight of phosphorus and up to 0.02 percent by weight of sulphur, is also suitable.

Surprisingly, it is not necessary to add esterification catalysts in the distillation. However, small amounts of an esterification catalyst can also be added. Catalysts which can be admixed are, for example, sulphuric acid, phosphoric acid, polyphosphoric acid or sulphonic acids.

The mixture of carboxylic acid and propylene glycol diester obtained as the sump product from the distillation column when the process according to the invention is carried out can easily be separated into the individual components. In general, the carboxylic acid is distilled off from the dicarboxylate in a further distillation. The propylene glycol dicarboxylate can then be subjected in a known manner, for example by vacuum distillation, to final purification until the desired purity is obtained.

In a particular embodiment of the process according to the invention, for example, a benzene solution containing about 15 to 25 percent by weight of perpropionic acid is employed for epoxidation of the propylene. The water content of this solution is 0.1 to 2 percent by weight. The solution of perpropionic acid in benzene is reacted with propylene, using a molar ratio of perpropionic acid to propylene of 1:2 to 3, at a temperature of 60° to 80° C. and at a pressure of 6 to 12 bars. 3 stirred kettles arranged in a cascade are used, for example, as the reaction vessel and the reaction is carried out in these with a residence time of 1.5 to 3 hours. The conversion of the perpropionic acid is 98 to 100%. The selectivity of the reaction for propylene oxide is 90 to 98%. About 1 to 6 mol % of propylene glycol, propylene glycol monopropionate and propylene glycol dipropionate are formed, relative to the amount of propylene oxide. The composition of the reaction mixture is about 8 to 12 percent by weight of propylene oxide, 1 to 5 percent by weight of propylene, 20 to 35 percent by weight of propionic acid and 0.15 to 0.8 percent by weight of propylene glycol, propylene glycol monopropionate and propylene glycol dipropionate; the remainder is benzene.

Working up by distillation starts with separation into a top product of propylene oxide and propylene, which contains about 30 to 50% of benzene, and a sump product which contains the remainder of the benzene, the propionic acid and the by-products derived from propylene glycol. The product withdrawn from the sump of this distillation column is transferred to a second fractionation column, which is provided with a circulation reboiler and a condenser with a phase separator. At a pressure of 2 to 3 bars, benzene is distilled over the top, the water of esterification being separated from the condensate. Part of the upper phase of the condensate is returned to the column as reflux. The reflux ratio is 0.5 to 2. A solution of about 1 to 10 percent by weight of propylene glycol dipropionate in propionic acid is obtained as the sump product.

In a further distillation column, propionic acid is distilled off over the top at a pressure of 100 to 400 mm Hg. The propylene glycol dipropionate which is thus obtained as the sump product is isolated in a purity of more than 99% in a final fractionation column provided with a thin layer evaporator. It can be put directly to further use.

The advantage of the process according to the invention is that, in the preparation of propylene oxide from propylene and a percarboxylic acid, the propylene glycol dicarboxylate corresponding to the percarboxylic acid is isolated without any particular additional effort because of greater uniformity of the by-products derived from propylene glycol. The problem of the separation and/or suitable further use of the by-product mixture of propylene glycol and propylene glycol carboxylic acid esters, which is obtained with the processes known hitherto, is thus also eliminated.

DESCRIPTION OF PROCESS

Referring to the flow diagram, propylene is fed into a reactor to which is added perpropionic acid dissolved in benzene. The reaction product is removed from the reactor and introduced into distillation column I from which are removed as overhead propylene, propylene oxide and benzene. Other components of the reaction product are removed as bottoms. The overhead from distillation column I is fed into a second distillation column, distillation column II, to remove prop and propylene oxide overhead and benzene as bottoms. The benzene bottoms from distillation column II is mixed with the bottoms from distillation column I and the combined mass is introduced into distillation column III from which benzene is removed as overhead. The bottoms from distillation column II comprise propionic acid and propylene glycol dipropionate. These bottoms can be fed to distillation column IV wherein propionic acid is removed as overhead and propylene glycol dipropionate is removed as bottoms, optionally with return of a portion of distillation column III bottoms back into distillation column III.

EXAMPLE

In a reaction system, 7.4 kg pure hour of high purity propylene (=175.8 mols/hour) are epoxidised with 68.27 kg per hour of a benzene solution of perpropionic acid (20.48% by weight=155.2 mols/hour), which also contains 12.67% by weight of propionic acid, 0.16% by weight of hydrogen peroxide, less than 0.1% by weight of water and 250 mg/kg of a Na salt of a partially esterified polyphosphoric acid as the stabiliser.

The excess propylene, relative to the perpropionic acid feed, is 13.3 mol %. The reaction system consists of two loop reactors arranged in series and a downstream delay tube. The reaction is carried out at a pressure of 4 bars. All the propylene is fed into the first loop reactor. The reaction temperature in the two loop reactors is 65° C. and the average residence time of the reaction mixture is about 45 minutes in each case. In the delay tube, the reaction temperature is 70° C. and the average residence time of the reaction mixture is about 70 minutes. On leaving the second loop reactor, the perpropionic acid is about 90% converted and after the delay tube a conversion of 99.8% is achieved. The reaction mixture then contains on average 1.16% by weight of propylene, 11.8% by weight of propylene oxide, 26.5% by weight of propionic acid and about 0.2% by weight of propylene glycol monopropionate in addition to the solvent benzene.

This reaction mixture is directly let down into a distillation column (I), in which propylene, the whole of the propylene oxide and about 10% of the benzene are separated off as the distillate. In a distillation column (II), this distillate is separated into its components propylene, propylene oxide (8.91 kg/hour, 99.9% purity=98.7%, relative to the perpropionic acid employed) and benzene as the sump product.

The sump product from column (I) is combined with the sump product from column (II) and the combined products are fed into a distillation column (III). The combined product streams contain, on average, 30.5% by weight of propionic acid, 69.1% by weight of benzene, about 0.2% by weight of propylene glycol monopropionate as well as small amounts of propylene glycol and propylene glycol dipropionate.

Distillation column (III) is a packed column (length=6 m, diameter=150 mm), which is provided with a circulation reboiler, a condenser and a separator for phase separation of the distillate at the top of the column. The feed is in the centre of the column. At a pressure of 2.6 bars, a residence time of 80 minutes in the sump of the column, a sump temperature of 180° C., a temperature at the top of the column of 116° C. and a reflux ratio of about 1.0, 45.5 kg per hour of benzene (with 0.11% by weight of propionic acid and 0.09% by weight of water) are obtained. In the course of 24 hours, 0.5 kg of aqueous phase, which contains about 5% by weight of propionic acid, are obtained in the separator.

The sump product, which contains about 1% by weight of propylene glycol dipropionate, is fed to a distillation column (IV) (packed column, length=4 m, diameter=150 mm). At a pressure of 100 mm Hg, a sump temperature of 170° C., a temperature at the top of the column of 89° C. and a reflux ratio of about 0.2, 19.8 kg per hour of propionic acid (approximately 99.8% purity) are distilled off. 0.25 kg per hour of crude propylene glycol dipropionate are withdrawn from the sump of this column. This product is distilled batchwise at 50 mm Hg in a thin layer evaporator fitted with a packed column (length=2 m, diameter=100 mm), 0.22 kg of propylene glycol dipropionate of approximately 98% purity being obtained from 0.25 kg of the crude product. This amount corresponds to 0.75%, relative to the perpropionic acid employed.

We claim:

1. In a process for the production of propylene oxide wherein propylene is contacted with percarboxylic acid in an organic solvent to produce a reaction mixture comprising, in the solvent, 1–50 weight percent of propylene oxide and 1–50 weight percent of the carboxylic acid corresponding to the percarboxylic acid, propylene, and as by-product, up to 25 mol percent based upon the amount of propylene oxide of a mixture of propylene glycol, propylene glycol monocarboxylate and propylene glycol dicarboxylate, the carboxylate group of the by-product being of said carboxylic acid, said solvent being present in an amount of 20 to 90 weight percent, the boiling point of the solvent being lower than that of the carboxylic acid and higher than of propylene oxide, distilling the reaction mixture in a first distillation zone into an overhead fraction rich in propylene oxide and propylene and a bottoms fraction rich in the carboxylic acid, the by-product, and the solvent, the improvement which comprises, for the recovery of the by-product as propylene glycol dicarboxylate, in a second distillation zone, distilling the bottoms fraction at a pressure of 1.5–6 bars, a sump temperature of 130°–250° C., a reflux ratio of 0.2–10 and an average sump residence time of 10–90 minutes to form propylene glycol dicarboxylate and taking overhead a fraction rich in the solvent and a bottoms fraction rich in the carboxylic acid and the so-formed propylene glycol dicarboxylate virtually only propylene glycol dicarboxylate is formed under said distillation conditions and recovering propylene glycol dicarboxylate from the bottoms fraction of the second distillation zone.

2. Process of claim 1, wherein the carboxylate groups of the propylene glycol dicarboxylate contain 1 to 4 carbon atoms.

3. Process of claim 1, wherein the second distillation is carried out at a pressure of 2.5–4 bars and at a sump temperature of 160° to 190° C.

4. Process of claim 1, wherein the dicarboxylate is propylene glycol dipropionate.

5. Process of claim 1, wherein the percarboxylic acid is perpropionic acid, the carboxylic acid is propionic acid, and said carboxylates are of propionic acid.

6. Process of claim 1, wherein the organic solvent is benzene.

7. Process of claim 1, wherein the percarboxylic acid is perpropionic acid, the second distillation is performed at 2.5–4 bars and a sump temperature of 160°–190° C. and the organic solvent is benzene.

8. Process of claim 1, wherein said recovery of propylene glycol dicarboxylate is by distillation.

9. Process of claim 1, wherein said second distillation is performed in the absence of an esterification catalyst.

10. Process of claim 1, wherein in the second distillation the bottoms fraction from the first distillation is separated into said overhead fraction of the second distillation and said bottoms fraction of the second distillation and the overhead of the second distillation consists of substantially pure solvent and water of esterification.

* * * * *

UNITED STATES PATENT AND TRADEMARK OFFICE
CERTIFICATE OF CORRECTION

PATENT NO. : 4,159,925
DATED : July 3, 1979
INVENTOR(S) : Schreyer et al.

It is certified that error appears in the above—identified patent and that said Letters Patent are hereby corrected as shown below:

Column 1, line 6, "678,327" should read -- 678,827 --.
Column 4, line 50, "prevent" should read -- present --.
Column 9, line 62, "prop" should read -- propylene --.
Column 9, line 68, "II" should read -- III --.

Signed and Sealed this

Thirteenth Day of November 1979

[SEAL]

Attest:

RUTH C. MASON
Attesting Officer

LUTRELLE F. PARKER
Acting Commissioner of Patents and Trademarks